(12) United States Patent
Graeber et al.

(10) Patent No.: US 7,737,181 B2
(45) Date of Patent: *Jun. 15, 2010

(54) PHARMACEUTICAL COMPOSITIONS COMPRISING 0.3% BY WEIGHT OF 6-[3-(1-ADAMANTYL)-4-METHOXYPHENYL]-2-NAPHTHOIC ACID FOR THE TREATMENT OF DERMATOLOGICAL DISORDERS

(75) Inventors: Michael Graeber, Lawrenceville, NJ (US); Janusz Czernielewski, Boit (FR)

(73) Assignee: Galderma Research & Development, Biot (FR)

( * ) Notice: Subject to any disclaimer, the term of this patent is extended or adjusted under 35 U.S.C. 154(b) by 536 days.

This patent is subject to a terminal disclaimer.

(21) Appl. No.: 11/494,693

(22) Filed: Jul. 28, 2006

(65) Prior Publication Data

US 2007/0043119 A1 Feb. 22, 2007

Related U.S. Application Data

(63) Continuation-in-part of application No. 10/937,612, filed on Sep. 10, 2004, which is a continuation of application No. PCT/EP03/03246, filed on Mar. 12, 2003.

(60) Provisional application No. 60/370,223, filed on Apr. 8, 2002.

(30) Foreign Application Priority Data

Mar. 12, 2002 (FR) .................................. 02 03070

(51) Int. Cl.
- A01N 37/10 (2006.01)
- A01N 37/00 (2006.01)
- A01N 31/04 (2006.01)
- A61K 31/19 (2006.01)
- A61K 31/185 (2006.01)
- A61K 31/07 (2006.01)

(52) U.S. Cl. ....................... 514/569; 514/577; 514/725; 514/859

(58) Field of Classification Search ................. 514/569, 514/577, 725, 859
See application file for complete search history.

(56) References Cited

U.S. PATENT DOCUMENTS

| | | | |
|---|---|---|---|
| 4,717,720 A * | 1/1988 | Shroot et al. ................... 514/63 |
| 5,098,895 A | 3/1992 | Shroot et al. | |
| 5,212,303 A | 5/1993 | Shroot et al. | |
| RE34,440 E | 11/1993 | Shroot et al. | |
| 5,306,486 A * | 4/1994 | McCook et al. ............... 424/59 |
| 5,603,940 A | 2/1997 | Candau et al. | |
| 5,665,364 A * | 9/1997 | McAtee et al. .............. 424/401 |
| 6,383,505 B1 | 5/2002 | Kaiser et al. | |
| 6,413,536 B1 * | 7/2002 | Gibson et al. ............... 424/423 |
| 7,083,799 B1 | 8/2006 | Giacomoni | |
| 7,579,377 B2 | 8/2009 | Graeber et al. | |
| 7,642,288 B2 | 1/2010 | Graeber | |
| 2005/0059740 A1 | 3/2005 | Graeber et al. | |

FOREIGN PATENT DOCUMENTS

| | | |
|---|---|---|
| EP | 0 199 636 B1 | 10/1986 |
| EP | 0 487 973 A1 | 3/1996 |
| EP | 0 487 973 B1 | 3/1996 |
| FR | 2 730 930 A | 8/1996 |
| WO | WO 02/083086 A1 | 10/2002 |
| WO | WO 03/075908 A1 | 9/2003 |

OTHER PUBLICATIONS

Talukdar et al. Journal of Pharmaceutical Sciences, May 1996, vol. 85, No. 5, pp. 537-540.*

Seppicontrol A5, Aug. 2001, pp. 1-53.*

"Topical Formulary for Carbopol® Polymers", Noveon, Inc., The Specialty Chemicals Innovator, Pharmaceutical Polymers, pp. 1-25, Jan. 2002, Cleveland, Ohio.

Body Cream, Phytosan™, Formula No. 416.09.0077.

Jamoulle et al., "Follicular Penetration and Distribution of Topically Applied CD 271, a new Naphthoic Acid Derivative Intended for Topical Acne Treatment", *Journal of Investigative Dermatology*, (1990), 94(5), 731-732, published by Nature Publishing Group.

Allec et al., "Skin distribution and pharmaceutical aspects of adapalene gel," *J. Am. Acad. Dermatol.* (1997) 36:S119-S125, published by American Academy of Dermatology, Inc., US.

Shroot et al., "A New Concept of Drug Delivery for Acne", *Dermatology* (1998), 196:165-170, published by S. Karger AG, Switzerland.

Rolland et al., "Site-specific Drug Delivery to Pilosebaceous Structures Using Polymeric Microspheres", *Pharmaceutical Research* (1993), vol. 10, No. 12, 1738-1744, published by Plenum Publishing Corporation.

(Continued)

Primary Examiner—Sreeni Padmanabhan
Assistant Examiner—Samira Jean-Louis
(74) Attorney, Agent, or Firm—Buchanan Ingersoll & Rooney PC (57) ABSTRACT

Dermatological disorders having an inflammatory or proliferative component, notably common acne, are treated with topically applicable pharmaceutical compositions containing about 0.3% by weight of 6-[3-(1-adamantyl)-4-methoxyphenyl]-2-naphthanoic acid (adapalene) or salt thereof, formulated into pharmaceutically acceptable media therefor, advantageously formulated into topically applicable gels, preferably aqueous gels, creams, lotions or solutions.

36 Claims, 3 Drawing Sheets

OTHER PUBLICATIONS

Alirezai et al., "Etude Comparative de l'efficacité et de la tolérance de gels d'adapalène à 0,1 et 0,03 p. 100 et d'un gel de trétimoïne á 0,025 p. 100 dans le traitement de l'acné" (Efficacy and safety comparison study of 0.1 p. 100 and 0.03 p. 100 adapalene gels and tretinoin gel in the topical treatment of acne), *Ann. Dermatol. Venereol.* (1996), 123:165-170, published by Paris Masson, Paris, France.

Healy et al. "Acnevulgaris", *British Medical Journal*, 1994 vol. 308, Iss. 6932, pp. 2-9.

Czernielewski et al. "Adapalene biochemistry and the evolution of a new topical retinoid for treatment of acne", *Journal of European Academy of Dermatology and Venerology*, Dec. 2001, vol. 15, Supplement 3, pp. 5-12.

Differen Gel Data Sheet, available Nov. 1998, pp. 1-5.

International Search Report for corresponding PCT/EP03/03246, (WO 03/075908 A1), in English.

Protest Under 37 C.F.R. § 1.291 regarding U.S. Appl. No. 11/494,693 (US 2007/0043119) with attachments dated Jun. 14, 2008.

European Search Report for corresponding European Application EP 05 003144 (in English).

Minutes for Oral Proceedings for European Application EP 03712109 corresponding to parent U.S. Appl. No. 10/937,612.

Goldfarb et al. "Photographic assessment of the effects of adapalene 0.1% and 0.3% gels and vehicle in photodamaged skin," Abstract published in European Academy of Dermatology and Venereology JEADV (2000) 14 (Suppl. 1), 315, Wiley-Blackwell, Hoboken, New Jersey.

Kang et al. "Assessment of adapalene gel for the treatment of actinic keratoses and lentigines: A randomized trial," J. Am. Acad. Dermatol., Jul. 2003, pp. 83-90, American Academy of Dermatology, Inc., Schaumberg, Illinois.

File History of U.S.P. 5,098,895 Shroot et al.

File History of Reissue 34,440, Shroot et al.

Notification of Non-Entry of Protest, dated Aug. 29, 2008 in U.S. Appl. No. 11/494,693, filed Jul. 28, 2006.

\* cited by examiner

PHARMACEUTICAL COMPOSITIONS COMPRISING 0.3% BY WEIGHT OF 6-[3-(1-ADAMANTYL)-4-METHOXYPHENYL]-2-NAPHTHOIC ACID FOR THE TREATMENT OF DERMATOLOGICAL DISORDERS

CROSS-REFERENCE TO PARENT/PRIORITY/PCT AND PROVISIONAL APPLICATIONS

This application is a continuation-in-part of our earlier pending Application, Ser. No. 10/937,612, filed Sep. 10, 2004. This '612 application claims priority under 35 U.S.C. §119 of FR-02/03070, filed Mar. 12, 2002, and of provisional application Ser. No. 60/370,223, filed Apr. 8, 2002, and is a continuation of PCT/EP 03/03246 filed Mar. 12, 2003 and designating the United States (published in English on Sep. 18, 2003 as WO 03/075908 A1). Each of the above applications is hereby expressly incorporated by reference and each is assigned to the assignee hereof.

BACKGROUND OF THE INVENTION

1. Technical Field of the Invention

The present invention relates to novel pharmaceutical compositions comprising about 0.3% by weigh of 6-[3-(1-adamantyl)-4-methoxyphenyl]-2-naphthanoic acid, the chemical structure of which is as follows:

in particular dermatological compositions, for the treatment of dermatological ailments, disorders, conditions or afflictions having an inflammatory or proliferative component.

2. Description of Background and/or Related and/or Prior Art

6-[3-(1-Adamantyl)-4-methoxyphenyl]-2-naphthanoic acid (hereinafter referred to as adapalene) is a retinoid derived from naphthoic acid, having anti-inflammatory properties. This molecule has been the subject of development for the topical treatment of common acne and dermatoses sensitive to retinoids.

Adapalene is described in EP-0,199,636, and a process for synthesizing same is described in EP-0,358,574, both assigned to the assignee hereof.

The assignee hereof markets adapalene formulated at a weight concentration of 0.1% in the form of an alcoholic lotion, an aqueous gel and a cream. These compositions are suited for the treatment of acne.

SUMMARY OF THE INVENTION

Novel pharmaceutical compositions have now been developed containing adapalene at a weight concentration on the order of or about 0.3%, formulated into pharmaceutically acceptable media therefor, suited for the treatment (regime or regimen) of dermatological ailments, conditions or afflictions having an inflammatory or proliferative component. Specifically, it has now surprisingly been shown that, in addition to exhibiting better therapeutic efficacy compared to known compositions, the compositions according to the invention exhibit good tolerance, comparable to those of the known compositions with a lower concentration of active principle.

The results regarding tolerance observed in trials relating to photo-damaged skin (indication "photodamage"), obtained on individuals on average 65 years old, could not be exploited in the context of the present invention. Specifically, as regards use of adapalene on young individuals (in particular regarding acne with populations of teenagers or young adults), the skin exhibits very different physiopathological characteristics (presence of many lesions, in particular inflammatory lesions, modifying skin permeability, hypercornification of the follicular channel, immuno response, bacterial colonization of the skin (*P. acnes*), sebaceous hyperplasia with hyperseborrhea).

DETAILED DESCRIPTION OF BEST MODE AND SPECIFIC/PREFERRED EMBODIMENTS OF THE INVENTION

Thus, the present invention features pharmaceutical compositions comprising about 0.3% by weight of adapalene (6-[3-(1-adamantyl)-4-methoxyphenyl]-2-naphthanoic acid) relative to the total weight of the composition, or salts thereof, preferably in the form of aqueous gels. Such compositions are suited for the treatment (regime or regimen) of dermatological ailments, disorders or conditions having an inflammatory or proliferative component.

The term "adapalene salts" is intended to mean the salts formed with a pharmaceutically acceptable base, in particular organic bases such as sodium hydroxide, potassium hydroxide and aqueous ammonia, or organic bases such as lysine, arginine or N-methylglucamine.

The term "adapalene salts" is also intended to mean the salts formed with a pharmaceutically acceptable base, in particular in organic bases such as sodium hydroxide, potassium hydroxide and aqueous amonia, or organic bases such as lysine, arginine or N-methylglucamine.

The term "adapalene salts" is also intended to mean the salts formed with fatty amines such as dioctylamine and stearylamine.

The pharmaceutical compositions according to the invention are preferably applied topically.

Topically, the pharmaceutical compositions according to the invention are more particularly suited for treatment of the skin and the mucous membranes, and may be in the form of ointments, creams, milks, pomades, powders, impregnated pads, solutions, gels, sprays, lotions or suspensions. They may also be in the form of suspensions of microspheres or nanospheres or of lipid or polymeric vesicles, or of polymeric patches and hydrogels for controlled release. These compositions for topical application may be in anhydrous form, in aqueous form or in the form of an emulsion.

In a preferred embodiment of the invention, the pharmaceutical compositions according to the invention are in the form of a gel, preferably aqueous, a cream, a lotion or a solution.

Accordingly, this invention also features pharmaceutical compositions comprising about 0.3% by weight of adapalene (6-[3-(1-adamantyl)-4-methoxyphenyl]-2-naphthanoic acid) relative to the total weight of the composition, or salt thereof, formulated as creams.

This invention also features pharmaceutical compositions comprising about 0.3% by weight of adapalene (6-[3-(1-adamantyl)-4-methoxyphenyl]-2-naphthanoic acid) relative to the total weight of the composition, or salt thereof, formulated as lotions.

By "lotion" is intended a fluid emulsion of water-in-oil or oil-in-water type. Preferably, the lotions according to the invention do not comprise any alcohol, but may comprise at least one glycol; consequently, they are not alcoholic, but preferably glycolic.

Another embodiment of the invention features pharmaceutical compositions comprising about 0.3% by weight of adapalene (6-[3-(1-adamantyl)-4-methoxyphenyl]-2-naphthanoic acid) relative to the total weight of the composition, or salt thereof, formulated as solutions or spray solutions.

By "solution" is intended to a liquid composition at ambient temperature (20-30°) and comprises a single phase. Such compositions are preferably alcoholic or may comprise at least one glycol or lipophilic component.

In particular, the pharmaceutical composition may be an aqueous gel comprising at least one ingredient selected from among:

Carbomers, for example Carbopol 980 NF marketed by NOVEON;

polymeric emulsifying agents such as PEMULEN (crosspolymers acrylates/C10-30 alkyl acrylates, for example, PEMULEN TR1, PEMULEN TR2, CARBOPOL 1342, CARBOPOL 1382, Carbopol 981 or carbopol Ultrez marketed by the company NOVEON);

polysaccharidic biopolymers such as xanthan gum (for example, Keltrol T and Xantural 180 marketed by the company Kelco);

gums such as caroub gum, guar gum;

alginates;

modified celluloses such as hydroxyethylcellulose, methylcellulose, hydroxypropylcellulose (for example Natrosol HHX 250 marketed by the company Aqualon), hydroxypropylmethylcellulose and carboxymethylcellulose;

starch derived products such as Structure XL marketed by the company National Starch;

a mix of polysorbate 80 and isohexadecane and acrylamide/sodium acryloyidimethyltaurate (such as Simulgel 600); and humectants or pro-penetrant agents such as propylene glycol or equivalent, for example, glycerin and sorbitol, for example, alkylens and polyalkylenes glycols (C1 to CE) such as ethylene glycol, polyethylene glycol (2 to 20 monomers), propylene glycol, dipropylene glycol, butylene glycol, pentylene glycol, hexylene glycol. These latter could be oxyethylened or not (2 to 50 QE). Glycol ethers are also representative such as ethoxydiglycol, diethylene glycol monoethylether (tradename transcutol HP by GATTEFOSSE company), dipelargonate propylene glycol, propylene glycol laurate (tradename Lauroglycol by GATTEFOSSE company), Propylene glycol dicaprate dicaprylate (tradename Estol 1526 by UNIQEMA company); and the pro-penetrants such as fatty esters family, fatty acids or fatty alcohols or alcohols, for example, ethanol, dimethyl isosorbide (tradename Arlasolve DMI by UNIQEMA company), pyrrolidone methyl (tradename Pharmasolve by ISP company), oleic acid (tradename Oléine V2 by Stéarinerie Dubois company), PEG-8 capric/caprylic glycerids (tradename LAERASOL by GATTEFOSSE company) and oleic alcohol (tradename HD EUTANOL V PH by COGNIS company).

In particular, the pharmaceutical composition may be a cream comprising at least one ingredient selected from among:

mineral oils such as perhydrosqualene;

silicone oils such as cyclomethicone;

siliconed oily components such as siliconed fatty components;

non-siliconed fatty components such as vegetable, mineral, animal or synthetic oils;

tensioactive agents or emulsifying agents, preferably such as PEG-20 methyl glucose sequistearate or Methyl glucose sesquistearate.

Among the non-siliconed oily components, the common oils are representative such as paraffin oil, Vaseline (or petroleum jelly), almond oil, perhydrosqualene, apricot oil, wheat germs oil, sweet almond oil, calophyllum oil, palm oil, castor oil, avocado oil, jojoba oil, olive oil or cerales germs oil; fatty acids esters or fatty alcohols esters such as dodecyl octyl octanoates, alcohols or polyalcohols decanoates or ricinoleates; fatty acids triglycerides; glycerides; hydrogenated polyisobutene, solid at 25° C. hydrogenated oils; lanolines; solid at 25° C. fatty esters; adipate diisopropyl (tradename Crodamol DA by Croda company), PPG 15 stearyl ether (tradename Arlamol E by UNIQEMA company), octyl dodecanol (tradename Eutanol G by COGNIS company), Caprilic/capric triglycerides (tradename Miglyol 812N by SPCI company), C12-C15 alkyl benzoate (tradename Tegosoft TN by Degussa company).

As tensioactive agents or as emulsifying agents, several components are representative selected from among PEG-20 methyl glucose sequistearate (tradename GLUCAMATE SSE 20 by Amerchol company) or Methyl glucose sesquistearate (tradename GLUCATE SS by Amerchol company), unsaturated or saturated fatty acids esters, oleic acid or isostearic acid such as polyglycerin and isostearic acid esters (tradename LAMEFORM TGI by SIDOBRE-SINNOVA HENKEL company), sorbitan isostearate (tradename ARLACEL 987 by UNIQEMA company), sorbitan sesquioleate (tradename ARLACEL 83 by UNIQEMA company), sorbitan laurate (tradename SPAN 20 by UNIQEMA company), glycol and isostearic acid esters such as PEG-6 isostearate (tradename OLEPAL ISOSTEARIQUE by GATTEFOSSE company), sorbitol and oleic acid esters such as polysorbates (tradename TWEEN by UNIQEMA company), fatty alcohols ethers such as oleic acid and particularly glycol and oleic acid esters such as oleths (tradename BRIJ by UNIQEMA company), oxyethylenated sorbitan monostearate, fatty alcohols such as stearylic alcohol or cetylic alcohol and particularly selected from among macrogol 21 stearylether (tradename BRIJ 721 by UNIQEMA company), macrogol 2 stearylether (tradename BRIJ 72P by UNIQEMA company), glyceryl/PEG 100 stearate (tradename Arlacel 165FL by UNIQEMA company), ceteareth 20 (tradename Eumulgin B2 by COGNIS company), PEG-6 and PEG 32 palmitostearate (tradename TEFOSE 1500 by GATTEFOSSE company).

In particular, the pharmaceutical composition may be a lotion comprising at least one ingredient selected from among:
- humectant agent or pro-penetrant agent such as propylene glycol (or equivalent such as glycerin and sorbitol), polyethylene glycol, PEG400;
- mineral oils such as perhydrosqualene as previously described;
- lipophilic components such as Caprilic/capric triglycerides as previously described;
- emulsifying agents such as described, for example, PEG-20 methyl glucose sequistearate and methyl glucose sequistearate.

Also in particular, the pharmaceutical composition may be a solution or a spray solution comprising alcohol and at least one ingredient selected from among:
- humectant agent or pro-penetrant agent as described previously and preferably such as propylene glycol, polyethylene glycol, or PEG400;
- a lipophilic component, such as siliconed or non-siliconed fatty components or Caprilic/capric triglycerides.

Preferably in the form of gel, the composition has of following formula:

| | |
|---|---|
| Adapalene | 3 mg |
| Carbomer 940 (Carbopol 980 NF) | 11 mg |
| Disodium edetate | 1 mg |
| Methyl paraben | 2 mg |
| Poloxamer 124 | 2 mg |
| Propylene glycol | 40 mg |
| Sodium hydroxide: amount required to obtain a pH 5.0 +/− 0.3 | |
| Purified water | q.s g .1 |

The pharmaceutical compositions according to the invention may also comprise inert additives or combinations thereof, such as:
- wetting agents;
- flavor enhancers;
- preservatives such as para-hydroxybenzoic acid esters;
- stabilizers;
- moisture regulators;
- pH regulators;
- osmotic pressure modifiers;
- emulsifiers;
- UV-A and UV-B screening agents; and
- antioxidants, such as α-tocopherol, butylhydroxyanisole or butylhydroxytoluene, superoxide dismutase, ubiquinol or certain metal chelating agents.

Of course, those skilled in the art will take care to select the optional compound(s) to be added to these compositions in such a way that the advantageous properties intrinsically associated with the present invention are not, or are not substantially, adversely affected by the envisaged addition.

The pharmaceutical compositions according to the invention are suited for the treatment of dermatological ailments, conditions and afflictions having an inflammatory or proliferative component, selected from the group consisting of:
- common acne, comedones, polymorphous acne, nodulocystic acne, acne conglobata, secondary acne such as solar, drug-related or occupational acne;
- widespread and/or severe forms of psoriasis, ichtyoses and ichtyosiform states;
- Darier's disease;
- actinic keratoses;
- palmo plantar keratoderma and keratosis pilaris;
- leucoplasias and leucoplasiform states, lichen planus;
- any benign or malignant, severe and extensive dermatological preparations.

The compositions according to the invention are particularly suitable for the treatment of acne, such as common acne, and in particular for the treatment of common acne of moderate to moderately severe intensity.

Various formulations of compositions comprising 0.3% of adapalene will now be given, it being understood that same are intended only as illustrative and in nowise limitative. Also given are results showing the therapeutic effects of the compositions according to the invention and the good tolerance to same by the treated patients.

In said examples to follow, all parts and percentages are given by weight, unless otherwise indicated.

EXAMPLE 1

Formulation for Topical Administration

In this example, various specific topical formulations comprising 0.3% of adapalene are illustrated.

The adapalene of the present example was obtained from the company Sylachim.

(a) Cream:

| | |
|---|---|
| Adapalene | 3 mg |
| Carbomer 934 (B F Goodrich Carbopol 974) | 4.5 mg |
| Disodium edetate | 1 mg |
| PEG 20 methyl glucose sesquistearate | 35 mg |
| Methyl glucose sesquistearate | 35 mg |
| Glycerol | 30 mg |
| Methyl paraben | 2 mg |
| Cyclomethicone | 130 mg |
| Perhydrosqualene | 60 mg |
| Phenoxyethanol | 5 mg |
| Propyl paraben | 1 mg |
| Sodium hydroxide quantity required for pH 6.5 +/− 0.3 | |
| Purified water | q.s. g 1 |

(b) Alcoholic Solution:

| | |
|---|---|
| Adapalene | 3 mg |
| PEG 400 | 700 mg |
| Ethanol | q.s. mg 1 |

(c) Lotion: (% w/w)

| | |
|---|---|
| Adapalene | 0.30 |
| Methyl paraben | 0.15 |
| Simulgel 600 PHA | 1.00 |
| Steareth 21 | 3.00 |
| Glyceryl and PEG 100 stearate | 3.00 |
| Disodium edetate | 0.10 |
| Propyl paraben | 0.05 |
| Perhydrosqualene | 5.00 |
| Cetearyl isonananoate | 5.00 |
| Sodium Hydroxide 10% m/m | q.s. pH 5.5 ± 0.5 |
| Purified water | q.s. 100 |

(d) Lotion: (% w/w)

| Disodium EDTA | 0.1 |
|---|---|
| Methyl paraben | 0.2 |
| Glycerine | 7.0 |
| Carbopol 981 NF | 0.15 |
| Propyl paraben | 0.1 |
| Ceteareth 20 | 3.0 |
| Stearyl alcohol | 2.0 |
| Caprilic/capric triglycerides | 7 |
| Glyceryl and PEG 100 stearate | 3.0 |
| Cyclomethicone 5 | 6 |
| Poloxamer 124 | 0.2 |
| Propylene glycol | 4.0 |
| Adapalene | 0.3 |
| Simulgel 600 PHA | 1.0 |
| Solution aq. De NaOH 10% | 0.4 |
| Purified water | q.s. 100 |

(e) Lotion: (% w/w)

| EDTA disodium | 0.1 |
|---|---|
| Methyl paraben | 0.2 |
| Carbopol 980 NF | 0.15 |
| Carbapol 981 NF | 0.3 |
| Glycerine | 3.0 |
| Phenoxyethanol | 1.0 |
| Propyl paraben | 0.2 |
| Methyl glucose sesquistearate | 1.0 |
| PEG 20 methyl glucose sesquistearate | 5.0 |
| Caprilic/capric triglycerides | 6.0 |
| Dimethicone 20 cst | 1.0 |
| Poloxamer 124 | 0.2 |
| Propylene glycol | 4 |
| Adapalene | 0.3 |
| Sodium hydroxide 10% (w/w) | 0.8 |
| Purified water | q.s. 100 |

(f) Aqueous Gel:

| Adapalene | 3 mg |
|---|---|
| Carbomer 940 (Carbapol 980) | 11 mg |
| Disodium edetate | 1 mg |
| Methyl paraben | 2 mg |
| Poloxamer 124 | 2 mg |
| Propylene glycol | 40 mg |
| Sodium hydroxide: amount required to obtain a pH 5.0 +/− 0.3 | |
| Purified water | q.s g .1 |

(g) Aqueous Gel:

| Adapalene | 3 mg |
|---|---|
| Xanthan gum | 8 mg |
| Hydroxypropylethylcellulose | 10 mg |
| Disodium edetate | 1 mg |
| Methyl paraben | 2 mg |
| Phenoxyethanol | 10 mg |
| Poloxamer 124 | 2 mg |
| Propylene glycol | 40 mg |
| Purified water | q.s. g 1 |

(h) Cream Gel:

| Adapalene | 3 mg |
|---|---|
| Simulgel 600 PHA | 20 mg |
| Cetearyl isononanoate | 100 mg |
| Disodium edetate | 1 mg |
| Methyl paraben | 2 mg |
| Poloxamer 124 | 2 mg |
| Propylene glycol | 40 mg |
| Purified water | q.s. g 1 |

(i) Cream Gel:

| Adapalene | 3 mg |
|---|---|
| Pemulen TR1 | 5 mg |
| Mineral oil | 120 mg |
| Disodium edetate | 1 mg |
| Methyl paraben | 2 mg |
| Propyl paraben | 1 mg |
| Poloxamer 124 | 2 mg |
| Propylene glycol | 40 mg |
| Sodium hydroxide: amount required to obtain a pH 5.0 +/− 0.3 | |
| Purified water | q.s. g 1 |

(j) Spray Solution: (% w/w)

| Adapalene | 0.3 |
|---|---|
| Caprilic/capric triglycerides | 50 |
| N-methyl pyrrolidone | 3 |
| Ethanol | q.s. 100 |

EXAMPLE 2

Effectiveness of 0.3% Adapalene Gel and Comparison with 0.1% Adapalene Gel

Tests were carried out on a population consisting of patients suffering from acne. In this population, three groups were differentiated; the first received a daily topical application of the 0.3% adapalene gel, the second a daily topical application of the 0.1% adapalene gel in the same vehicle, and the third is a control group which receives a daily topical application of the gel corresponding to the composition of the first two gels but containing no active agent.

Figure 1:
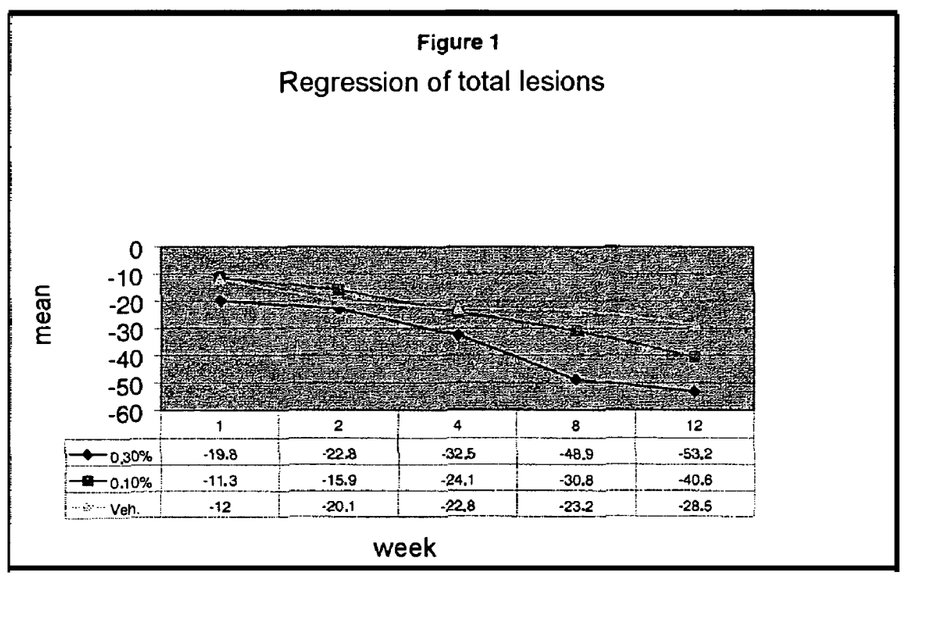
FIGS. 1-3 are graphs illustrating the effectiveness of the dermatological compositions of the present invention versus comparative compositions and controls.
Figure 2:
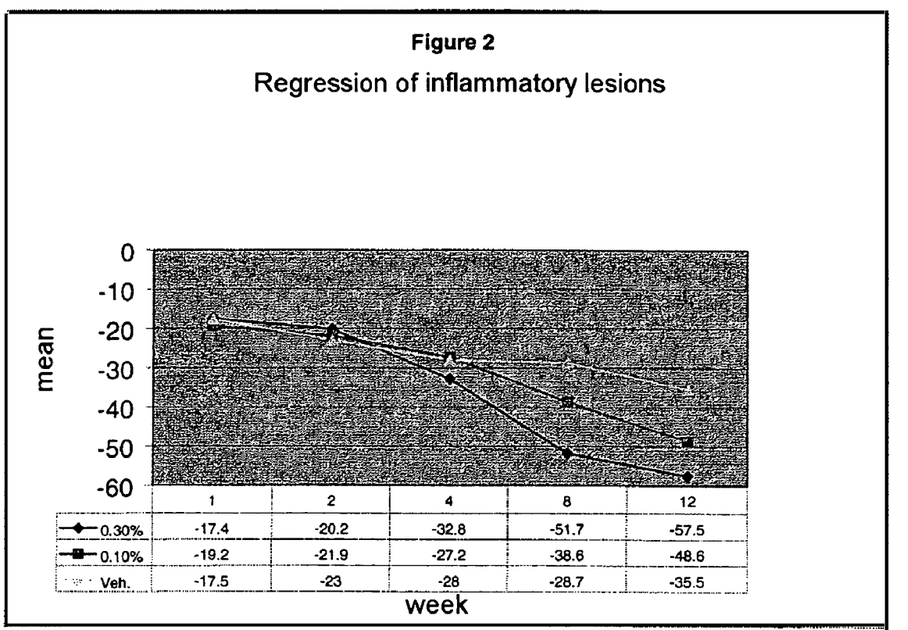
Figure 3:
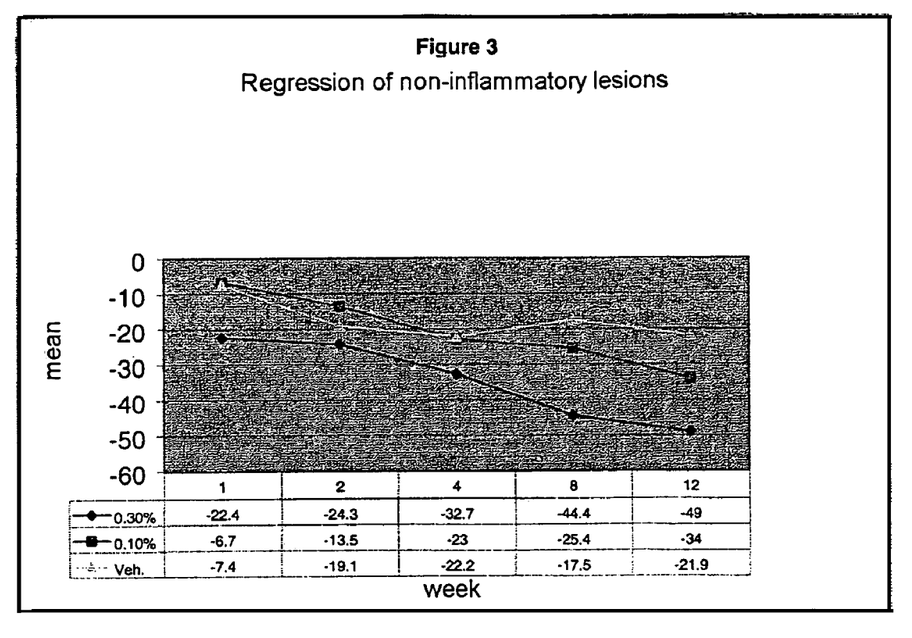

FIGS. 1 to 3 provide the results obtained in terms of regression of the number of lesions according to their nature.

These observations lead to the following conclusions:

the 0.3% adapalene gel acts more rapidly than the 0.1% adapalene gel; specifically, from the fourth week of treatment, a difference is noted between the effectiveness of the 0.1% adapalene gel and the 0.3% adapalene gel;

the 0.3% adapalene gel produces a clearly greater therapeutic effect after 8 weeks of treatment.

EXAMPLE 3

Tolerance Regarding the 0.3% Adapalene Gel

1. Measurement of the Plasma Concentration of Adapalene

Eight individuals suffering from common acne of medium to moderately severe intensity are treated for 10 days with 2 g of 0.3% adapalene gel applied daily over 1000 cm$^2$ of skin to be treated (face, chest and back).

Blood samples are taken on the days 1, 2, 4, 6, 8 and 10. During day 10, and following the final application, samples are taken at 1, 2, 6, 8, 10, 12, 16 and 24 hours.

The plasma concentration of total adapalene (free and conjugated) in these samples is determined using the following protocol:

- enzymatic hydrolysis with a mixture of β-glucurodinase and arylsulfatase;
- liquid-liquid extraction;
- passage through HPLC (high performance liquid chromatography); and
- then fluorometric detection.

This method makes it possible to detect a minimum concentration of 0.15 ng/ml and permits quantification of the adapalene for a minimum concentration of 0.25 ng/ml.

Conclusion:

The plasma concentrations of adapalene measured after 10 days of treatment are very low and confirm the safety of daily use of the 0.3% adapalene gel.

2 a) Clinical Observation of the Side Effects Caused by Topical Administration of the 0.3% Adapalene Gel Two types of observation could be made:

firstly, monitoring of the patients treated within the framework of point 1 of the present example 3 made it possible to note that tolerance to the 0.3% adapalene gel was good for all patients. They all showed signs of dryness of the skin and of desquamation with a maximum on the seventh day of treatment, these symptoms then decrease up to the end of the treatment.

2 b) Furthermore, Reference May Also be Made to the Tests Described in Example 2 Above In parallel to the measurements of effectiveness, the experimenters recorded the possible side effects caused, firstly, by topical application of the 0.3% adapalene gel and those caused, secondly, by application of the 0.1% adapalene gel; finally, the same observations were made on a control population to which a gel without active principle was administered.

These observations are reported in the table below.

| Local undesirable effects | 0.3% adapalene gel (N = 70) | 0.1% adapalene gel (N = 70) | Vehicle gel (N = 74) |
|---|---|---|---|
| Skin and secondary structures (nails, hair) | 31 (44.3%) | 28 (40.0%) | 5 (6.8%) |
| Dry skin | 16 (22.9%) | 13 (18.6%) | 2 (2.7%) |
| Erythema | 8 (11.4%) | 3 (4.3%) | 0 (0.0%) |
| Skin discomfort | 8 (11.4%) | 7 (10.0%) | 0 (0.0%) |
| Desquamation | 6 (8.6%) | 5 (7.1%) | 0 (0.0%) |
| Dermatitis | 3 (4.3%) | 1 (1.4%) | 0 (0.0%) |
| Pruritus | 3 (4.3%) | 1 1.4%) | 1 (1.4%) |
| Irritant dermatitis | 2 (2.9%) | 7 (10.0%) | 0 (0.0%) |
| Local allergic reactions | 1 (1.4%) | 0 (0.0%) | 0 (0.0%) |
| Pediculosis | 1 (1.4%) | 0 (0.0%) | 0 (0.0%) |
| Contact dermatitis | 1 (1.4%) | 0 (0.0%) | 0 (0.0%) |
| Insolation | 1 (1.4%) | 3 (4.3%) | 1 (1.4%) |
| Burning sensation | 1 (1.4%) | 0 (0.0%) | 0 (0.0%) |
| Urticaria | 1 1.4%) | 0 (0.0%) | 0 (0.0%) |
| Infection | 1 (1.4%) | 0 (0.0%) | 0 (0.0%) |
| Excoriation | 0 (0.0%) | 0 (0.0%) | 1 (1.4%) |
| Eczema | 0 (0.0%) | 0 (0.0%) | 1 (1.4%) |
| Oedema | 0 (0.0%) | 1.(1.4%) | 0 (0.0%) |

From this table, it is noted that the occurrence of undesirable side effects is statistically the same for the two gels with the different concentrations of active agent. The intensity of the undesirable side effects is average, which leads to the conclusion that the two gels are well-tolerated by the patients.

On the basis of these observations, it may be concluded that patients suffering from common acne can be treated with 0.3% adapalene gel, such an exposure to adapalene being described as weak or very weak under clinical conditions.

It therefore ensues from these various studies that a pharmaceutical composition containing 0.3% of adapalene exhibits a benefit/risk ratio which makes it particularly suitable for the treatment of dermatological maladies having an inflammatory or proliferative component, and in particular, common acne.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable pharmaceutical aqueous gel composition useful for the treatment of common acne, consisting essentially of an anti-acne effective amount of 6-[3-(1-adamantyl)-4-methoxyphenyl]-2-naphthanoic acid (adapalene) of 0.3% by weight thereof, formulated into a topically applicable, pharmaceutically acceptable aqueous gel medium therefor, wherein adapalene is the only active anti-acne ingredient in the composition and wherein said aqueous gel medium comprises at least one ingredient selected from the group consisting of carbomers, polymeric emulsifying agents, polysaccharidic biopolymers, gums, alginates, modified celluloses, starch derived products, mix of polysorbate 80 and isohexadecane and acrylamide/sodium acryloyldimethyltaurate, and mixtures thereof.

2. The topically applicable aqueous gel composition as defined by claim 1, wherein said aqueous gel medium comprises:

Carbomer,

Disodium edetate,

Methyl paraben,

Poloxamer 124,

Propylene glycol,

Sodium hydroxide, and

Purified water.

3. A topically applicable pharmaceutical aqueous gel composition useful for the treatment of common acne, consisting essentially of:

| | |
|---|---|
| Adapalene | 3 mg |
| Carbomer 940 | 11 mg |
| Disodium edetate | 1 mg |
| Methyl paraben | 2 mg |
| Poloxamer 124 | 2 mg |
| Propylene glycol | 40 mg |
| Sodium hydroxide: amount required to obtain a pH 5.0 +/− 0.3 and | |
| Purified water | q.s. 1 g. | wherein adapalene is the only active anti-acne ingredient in the composition.

4. The topically applicable aqueous gel composition as defined by claim 1, wherein said aqueous gel medium comprises:

| |
|---|
| Xanthan gum |
| Hydroxypropylethylcellulose |
| Disodium edetate |
| Methyl paraben |
| Phenoxyethanol |
| Poloxamer 124 |
| Propylene glycol |
| Purified water. |

5. A topically applicable pharmaceutical aqueous gel composition useful for the treatment of common acne, consisting essentially of:

| | |
|---|---|
| Adapalene | 3 mg |
| Xanthan gum | 8 mg |
| Hydroxypropylethylcellulose | 10 mg |
| Disodium edetate | 1 mg |
| Methyl paraben | 2 mg |
| Phenoxyethanol | 10 mg |
| Poloxamer 124 | 2 mg |
| Propylene glycol | 40 mg |
| Purified water | q.s. 1 g, | wherein adapalene is the only active anti-acne ingredient in the composition.

6. A topically applicable pharmaceutical aqueous cream gel composition useful for the treatment of common acne, consisting essentially of an anti-acne effective amount of 6-[3-(1-adamantyl)-4-methoxyphenyl]-2-naphthanoic acid (adapalene) of 0.3% by weight thereof, formulated into a topically applicable, pharmaceutically acceptable aqueous cream gel medium therefor, wherein adapalene is the only active anti-acne ingredient in the composition.

7. The topically applicable aqueous cream gel composition as defined by claim 6, comprising wherein said aqueous cream gel medium comprises:

| |
|---|
| Adapalene, |
| Simulgel 600 PHA |
| Cetearyl isononanoate |
| Disodium edetate, |
| Methyl paraben, |
| Poloxamer 124, |
| Propylene glycol, |
| Purified water. |

8. A topically applicable pharmaceutical aqueous cream gel composition useful for the treatment of common acne, consisting essentially of:

| | |
|---|---|
| Adapalene | 3 mg |
| Simulgel 600 PHA | 20 mg |
| Cetearyl isonananoate | 100 mg |
| Disodium edetate | 1 mg |
| Methyl paraben | 2 mg |
| Poloxamer 124 | 2 mg |
| Propylene glycol | 40 mg |
| Purified water | q.s. 1 g, | wherein adapalene is the only active anti-acne ingredient in the composition.

9. The topically applicable aqueous cream gel composition as defined by claim 6, wherein said aqueous cream gel medium comprises:

| |
|---|
| Adapalene |
| Pemulen TR1 |
| Mineral Oil |
| Disodium edetate |
| Methyl paraben |
| Proply paraben |
| Poloxamer 124 |
| Sodium hydroxide: amount required to obtain a pH 5.0 +/− 0.3 |
| Purified water. |

10. A topically applicable pharmaceutical aqueous cream gel composition useful for the treatment of common acne, consisting essentially of:

| | |
|---|---|
| Adapalene | 3 mg |
| Pemulen TR1 | 5 mg |
| Mineral oil | 120 mg |
| Disodium edetate | 1 mg |
| Methyl paraben | 2 mg |
| Propyl paraben | 1 mg |
| Poloxamer 124 | 2 mg |
| Propylene glycol | 40 mg |
| Sodium hydroxide: amount required to obtain a pH 5.0 +/− 0.3 | |
| Purified water | q.s. 1 g, | wherein adapalene is the only active anti-acne ingredient in the composition.

11. A topically applicable pharmaceutical cream composition useful for the treatment of common acne, consisting essentially of an anti-acne effective amount of 6-[3-(1-adamantyl)-4-methoxyphenyl]-2-naphthanoic acid (adapalene) of 0.3% by weight thereof, formulated into a topically applicable, pharmaceutically acceptable cream medium therefor, wherein adapalene is the only active anti-acne ingredient in the composition.

12. The topically applicable cream composition as defined by claim 11, wherein said cream medium comprises at least one ingredient selected from the group consisting of silicone oils, siliconed oily substances, siliconed fatty substances, non-siliconed fatty substances, vegetable oils, mineral oils, animal oils and synthetic oils, and mixtures thereof.

13. The topically applicable cream composition as defined by claim 12, wherein said cream medium comprises at least one ingredient selected from the group consisting of perhy- 14. The topically applicable cream composition as defined by claim 11, wherein said cream medium comprises:

| |
|---|
| Adapalene |
| Carbomer 934 (BF Goodrich Carbopol 974) |
| Disodium edetate |
| PEG 20 methyl glucose sesquistearate |
| Methyl glucose sesquistearate |
| Glycerol |
| Methyl paraben |
| Cyclomethicone |
| Perhydrosqualene |
| Phenoxyethanol |
| Propyl paraben |
| Sodium hydroxide quantity required for pH 6.5 +/− 0.3 |
| Purified water. |

15. A topically applicable pharmaceutical cream composition useful for the treatment of common acne, consisting essentially of:

| | |
|---|---|
| Adapalene | 3 mg |
| Carbomer 934 (BF Goodrich Carbopol 974) | 4.5 mg |
| Disodium edetate | 1 mg |
| PEG 20 methyl glucose sesquistearate | 35 mg |
| Methyl glucose sesquistearate | 35 mg |
| Glycerol | 30 mg |
| Methyl paraben | 2 mg |
| Cyclomethicone | 130 mg |
| Perhydrosqualene | 60 mg |
| Phenoxyethanol | 5 mg |
| Propyl paraben | 1 mg |
| Sodium hydroxide quantity required for pH 6.5 +/− 0.3 | |
| Purified water | q.s. 1 g, | wherein adapalene is the only active anti-acne ingredient in the composition.

16. A topically applicable pharmaceutical aqueous lotion composition useful for the treatment of common acne consisting essentially of an anti-acne effective amount of 6-[3-(1-adamantyl)-4-methoxyphenyl]-2-naphthanoic acid (adapalene) of 0.3% by weight thereof, formulated into a topically applicable, pharmaceutically acceptable aqueous lotion medium therefor, wherein adapalene is the only active anti-acne ingredient in the composition.

17. The topically applicable aqueous lotion composition as defined by claim 16, wherein said aqueous lotion medium comprises at least one ingredient selected from the group consisting of humectant agent, pro-penetrant agent, propylene glycol, PEG400, mineral oils, lipophilic substances, caprilic/capric triglycerides, emulsifying agent, and mixtures thereof.

18. The topically applicable aqueous lotion composition as defined by claim 16, wherein said aqueous lotion medium comprises at least one ingredient selected from the group consisting of propylene glycol, glycerine, sorbitol, polyethylene glycol, mineral oils, perhydrosqualene, caprilic/capric triglycerides, PEG-20 methyl glucose sequistearate, methyl glucose sequistearate, and mixtures thereof.

19. The topically applicable aqueous lotion composition as defined by claim 16, wherein said aqueous lotion medium comprises:

| |
|---|
| Adapalene |
| Methyl paraben |
| Simulgel 600 PHA |
| Steareth 21 |
| Glyceryl and PEG 100 stearate |
| Disodium edetate |
| Propyl paraben |
| Perhydrosqualene |
| Cetearyl isononanoate |
| Sodium Hydroxide 10% m/m |
| Purified water. |

20. A topically applicable pharmaceutical aqueous lotion composition useful for the treatment of common acne, consisting essentially of:

| | (% w/w) |
|---|---|
| Adapalene | 0.30 |
| Methyl paraben | 0.15 |
| Simulgel 600 PHA | 1.00 |
| Steareth 21 | 3.00 |
| Glyceryl and PEG 100 stearate | 3.00 |
| Disodium edetate | 0.10 |
| Propyl paraben | 0.05 |
| Perhydrosqualene | 5.00 |
| Cetearyl isononanoate | 5.00 |
| Sodium Hydroxide 10% m/m | q.s. pH 5.5 ± 0.5 |
| Purified water | q.s. 100, | wherein adapalene is the only active anti-acne ingredient in the composition.

21. The topically applicable aqueous lotion composition as defined by claim 16, wherein said aqueous lotion medium comprises:

| |
|---|
| Disodium EDTA |
| Methyl paraben |
| Glycerine |
| Carbopol 981 NF |
| Propyl paraben |
| Ceteareth 20 |
| Stearyl alcohol |
| Caprilic/capric triglycerides |
| Glyceryl and PEG 100 stearate |
| Cyclomethicone 5 |
| Poloxamer 124 |
| Propylene glycol |
| Simulgel 600 PHA |
| Solution aq. De NaOH 10% |
| Purified water. |

22. A topically applicable pharmaceutical aqueous lotion composition useful for the treatment of common acne, consisting essentially of:

| | (% w/w) |
|---|---|
| Disodium EDTA | 0.1 |
| Methyl paraben | 0.2 |
| Glycerine | 7.0 |
| Carbopol 981 NF | 0.15 |
| Propyl paraben | 0.1 |
| Ceteareth 20 | 3.0 |
| Stearyl alcohol | 2.0 |
| Caprilic/capric triglycerides | 7 |

-continued

|  | (% w/w) |
| --- | --- |
| Glyceryl and PEG 100 stearate | 3.0 |
| Cyclomethicone 5 | 6 |
| Poloxamer 124 | 0.2 |
| Propylene glycol | 4.0 |
| Adapalene | 0.3 |
| Simulgel 600 PHA | 1.0 |
| Solution aq. De NaOH 10% | 0.4 |
| Purified water | q.s. 100, | wherein adapalene is the only active anti-acne ingredient in the composition.

23. The topically applicable aqueous lotion composition as defined by claim 16, wherein said aqueous lotion medium comprises:

EDTA disodium
Methyl paraben
Carbopol 980 NF
Carbopol 981 NF
Gylcerine
Phenoxyethanol
Propyl paraben
Methyl glucose sesquistearate
PEG 20 methyl glucose sesquistearate
Caprilic/capric triglycerides
Dimethicone 20 cst
Poloxamer 124
Propylene glycol
Sodium Hydroxide 10% m/m
Purified water.

24. A topically applicable pharmaceutical aqueous lotion composition useful for the treatment of common acne consisting essentially of:

|  | (% w/w) |
| --- | --- |
| Disodium EDTA | 0.1 |
| Methyl paraben | 0.2 |
| Glycerine | 7.0 |
| Carbopol 981 NF | 0.15 |
| Propyl paraben | 0.1 |
| Ceteareth 20 | 3.0 |
| Stearyl alcohol | 2.0 |
| Caprilic/capric triglycerides | 7 |
| Glyceryl and PEG 100 stearate | 3.0 |
| Cyclomethicone 5 | 6 |
| Poloxamer 124 | 0.2 |
| Propylene glycol | 4.0 |
| Adapalene | 0.3 |
| Simulgel 600 PHA | 1.0 |
| Solution aq. De NaOH 10% | 0.4 |
| Purified water | q.s. 100, | wherein adapalene is the only active anti-acne ingredient in the composition.

25. A topically applicable pharmaceutical spray solution composition useful for the treatment of common acne consisting essentially of an anti-acne effective amount of 6-[3-(1-adamantyl)-4-methoxyphenyl]-2-naphthanoic acid (adapalene) of 0.3% by weight thereof, formulated into a topically applicable, pharmaceutically acceptable spray solution medium therefor, said spray solution medium comprising caprilic/capric triglycerides, wherein adapalene is the only active anti-acne ingredient in the composition.

26. The topically applicable spray solution composition as defined by claim 25, wherein said spray solution medium further comprises at least one ingredient selected from the group consisting of humectant agent, pro-penetrant agent, propylene glycol, polyethylene glycol, PEG400, a lipophilic substance, siliconed fatty substances, non-siliconed fatty substances, and mixtures thereof.

27. The topically applicable spray solution composition as defined by claim 25, wherein said spray solution medium comprises:
Caprilic/capric triglycerides,
N-methyl pyrrolidone, and
Ethanol.

28. A topically applicable pharmaceutical spray solution composition useful for the treatment of common acne, consisting essentially of:

|  | (% w/w) |
| --- | --- |
| Adapalene | 0.3 |
| Caprilic/capric triglycerides | 50 |
| N-methyl pyrrolidone | 3 |
| Ethanol | q.s. 100, | wherein adapalene is the only active anti-acne ingredient in the composition.

29. The topically applicable aqueous gel composition as defined by claim 1, wherein said aqueous gel medium comprises at least one inert additive selected from the group consisting of:
wetting agents;
flavor enhancers;
preservatives;
stabilizers;
moisture regulators;
pH regulators;
osmotic pressure modifiers;
emulsifiers;
UV-A and UV-B screening agents;
Antioxidants; and
combinations thereof.

30. The topically applicable aqueous cream gel composition as defined by claim 6, wherein said aqueous cream gel medium comprises at least one inert additive selected from the group consisting of:
wetting agents;
flavor enhancers;
preservatives;
stabilizers;
moisture regulators;
pH regulators;
osmotic pressure modifiers;
emulsifiers;
UV-A and UV-B screening agents;
Antioxidants; and
combinations thereof.

31. The topically applicable cream composition as defined by claim 11, wherein said cream medium comprises at least one inert additive selected from the group consisting of:
wetting agents;
flavor enhancers;
preservatives;
stabilizers;
moisture regulators;

pH regulators;
osmotic pressure modifiers;
emulsifiers;
UV-A and UV-B screening agents;
Antioxidants; and
combinations thereof.

32. The topically applicable aqueous lotion composition as defined by claim 16, wherein said aqueous lotion medium comprises at least one inert additive selected from the group consisting of:
wetting agents;
flavor enhancers;
preservatives;
stabilizers;
moisture regulators;
pH regulators;
osmotic pressure modifiers;
emulsifiers;
UV-A and UV-B screening agents;
Antioxidants; and
combinations thereof.

33. The topically applicable spray solution composition as defined by claim 25, wherein said spray solution medium comprises at least one inert additive selected from the group consisting of:
wetting agents;
flavor enhancers;
preservatives;
stabilizers;
moisture regulators;
pH regulators;
osmotic pressure modifiers;
emulsifiers;
UV-A and UV-B screening agents;
Antioxidants; and
combinations thereof.

34. The topically applicable pharmaceutical aqueous lotion composition useful for the treatment of common acne, consisting essentially of:

|  | (% w/w) |
|---|---|
| EDTA disodium | 0.1 |
| Methyl paraben | 0.2 |
| Carbopol 980 NF | 0.15 |
| Carbopol 981 NF | 0.3 |
| Gylcerine | 3.0 |
| Phenoxyethanol | 1.0 |
| Propyl paraben | 0.2 |
| Methyl glucose sesquistearate | 1.0 |
| PEG 20 methyl glucose sesquistearate | 5.0 |
| Caprilic/capric triglycerides | 6.0 |
| Dimethicone 20 cst | 1.0 |
| Poloxamer 124 | 0.2 |
| Propylene glycol | 4 |
| Adapalene | 0.3 |
| Sodium Hydroxide 10% m/m | 0.8 |
| Purified water | q.s. 100. |

35. The topically applicable aqueous gel composition as defined by claim 1, wherein said aqueous gel medium comprises at least one carbomer.

36. The topically applicable aqueous gel composition as defined by claim 1, wherein said aqueous gel medium comprises carbomer 940.

* * * * *